United States Patent [19]

D'Amico

[11] 4,362,547

[45] * Dec. 7, 1982

[54] IMIDES DERIVED FROM 2-THIOXO-3-BENZOX(THIA)AZOLINE ACETIC, AND PROPIONIC ACIDS

[75] Inventor: John J. D'Amico, Olivette, Mo.

[73] Assignee: Monsanto Company, St. Louis, Mo.

[*] Notice: The portion of the term of this patent subsequent to Sep. 8, 1998, has been disclaimed.

[21] Appl. No.: 223,637

[22] Filed: Jan. 9, 1981

Related U.S. Application Data

[62] Division of Ser. No. 55,103, Jul. 5, 1979.

[51] Int. Cl.³ ............................................. A01N 43/78
[52] U.S. Cl. ........................................ 71/90; 548/165; 548/221; 71/88
[58] Field of Search ............................................. 71/90

[56] References Cited

U.S. PATENT DOCUMENTS 4,228,292  10/1980  D'Amico ................................ 71/90

FOREIGN PATENT DOCUMENTS 22353  5/1979  European Pat. Off. ................ 71/90
 7772  2/1980  European Pat. Off. ................ 71/90

*Primary Examiner*—David B. Springer
*Attorney, Agent, or Firm*—Stanley M. Tarter; Howard C. Stanley

[57] ABSTRACT

Imides derived from 2-thioxo-3-benzothiazoline acetic and propionic have been found to be effective as herbicides and plant growth regulants.

1 Claim, No Drawings

IMIDES DERIVED FROM 2-THIOXO-3-BENZOX(THIA)AZOLINE ACETIC, AND PROPIONIC ACIDS

This is a division of application Ser. No. 55,103 filed July 5, 1979.

This invention relates to imides derived from 2-thioxo-3-benzothiazoline acetic acid and 2-thioxo-3-benzothiazoline propionic acid and their use as herbicides and plant growth regulants. In addition, imides derived from 2-thioxo-3-benzoxazoline acetic acid and 2-thioxo-3-benzoxazoline propionic acid are effective as plant growth regulants. More specifically, the invention relates to compounds having the formula

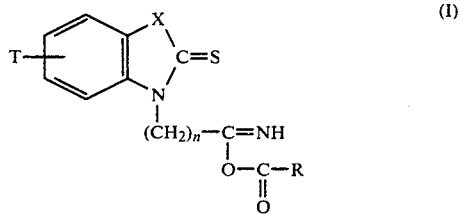

wherein X is sulfur or oxygen, R is lower alkyl, T is hydrogen halogen, nitro, lower alkyl or trifluoromethyl and n is one or two.

The term "lower alkyl" as used herein is understood to include those alkyl groups having up to five carbon atoms inclusive. Both straight as well as branched chain alkyl groups are contemplated.

The term "halogen" as used herein includes chlorine, bromine, fluorine and iodine.

The imides of the foregoing formula are prepared by reaction of the appropriate amide with an anhydride in accordance with the following reaction scheme:

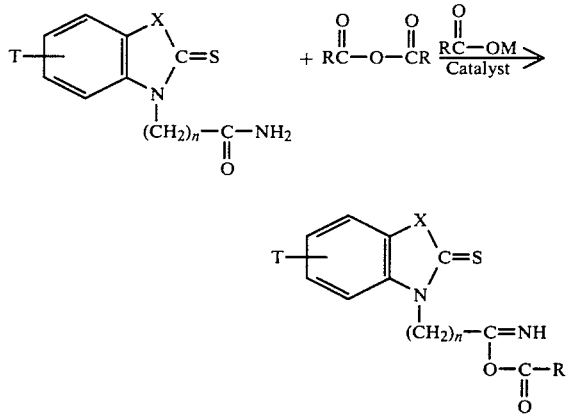

It has been found that a catalyst consisting of the alkali metal salt of a lower alkanoic acid having the formula

must be utilized. In the above formula, M represents an alkali metal.

The amide precursor may be prepared in accordance with the procedure disclosed in co-pending application Ser. No. 55,103 entitled "N-Substituted Thioxobenzothiazoline Derivatives And Their Use As Plant Growth Regulants" by J. J. D'Amico filed July 5, 1979. As disclosed therein the amide precursor (wherein n is 1) may be prepared by the reaction of ammonia with ethyl ester of 2-thioxo-3(2H)-benzothiazole acetic acid in ammonium hydroxide. Where X is oxygen the ethyl ester of 2-thioxo-3-(2H)-benzoxazole acetic acid should be used. These esters may be prepared in accordance with the procedure described by CH Chen, ORGANIC PREPARATIONS AND PROCEDURES, INT 8(1), 1–5 (1976). To illustate this procedure, the following example is presented.

EXAMPLE 1

To a stirred slurry, at 25°–30° C., containing 70.0 g (0.276 mol) of ethyl ester of 2-thioxo-3(2H)-benzothiazole acetic acid in 800 ml of concentrated ammonia hydroxide, ammonia gas was bubbled into the slurry for two to three hours each day for a total period of 4 days. The product, 2-thioxo-3(2H)-benzothiazole-acetamide, was collected by filtration, washed with water until neutral to litmus and air-dried at 50° C., mp 277°–278° C., yield 91%.

Anal. Calc'd for $C_9H_8N_2OS_2$: C,48.19; H,3.60; N,12.49; S,28.59. Found: C,48.16; H,3.61; N,12.49; S,28.50.

When n is 2 the precursor amide may be prepared by reaction of 2-mercaptobenzothiazole or 2-mercaptobenzoxazole with acrylamide in a base such as triethylamine. Illustrative of this process is the following examples.

EXAMPLE 2(a)

To a stirred solution at 50° C. containing 86 g (0.5 mol) of 2-mercaptobenzothiazole, 60.8 g (0.6 mol) of triethylamine and 500 ml of water, 43 g (0.6 mol) of acrylamide was added in one portion. After stirring at 60°–70° C. for 24 hours, the stirred reaction mixture was cooled to 25° C., the solid collected by filtration, washed with water until neutral and air-dried at 50° C. The product, 2-thioxo-3(2H)-benzothiazolepropanamide, mp 226°–227° C. was obtained in 77% yield.

Anal Calc'd for $C_{10}H_{10}N_2OS_2$: C,50.40; H,4.23; N,11.75; S,26.91. Found: C,50.28; H,4.28; N,11.72; S,26.79

EXAMPLE 2(b)

Employing the same procedure as described in example 2(a) except 75.2 g (0.2 mol) of 2-mercaptobenoxazole was used, furnished the product, 2-thioxo-3-(2H)benzoxazole propanamide, mp 203°–204° C., in 42% yield. After recrystallization from DMF it melted at 208°–209° C.

Anal. Calc'd for $C_{10}H_{10}N_2O_2S$: C,54.04; H,4.54; N,12.60; S,14.43. Found: C,54.01; H,4.55; N,12,59; S,14.44.

As noted above, the imides may be prepared by reaction of 2-thioxo-3(2H)-benzothiazole acetamide or propanamide, 2-thioxo-3(2H)-benzoxazole acetamide or propanamide with an anhydride. Generally, the procedure which may be utilized is as follows:

A Stirred slurry containing 0.1 mol of the appropriate amide, 150 to 250 ml of acetic, propionic, butyric or pentanoic anhydride and 2 g of sodium acetate, propionate, butyrate or pentenoate is heated at reflux (138°–140° C.) for 2 hours. During this period a solution is formed. After cooling the stirred solution to 5° C., 800 g of ice water is added and stirring continued at 0°–10° C. for 1 to 2 hours. The solid is collected by filtration, washed with water until neutral to litmus and air-dried at 25°–30° C. The data are summarized in Table I below.

gules of various plant species which are compacted to soil level. The soil required to level fill the pans after seeding or adding vegetative propagules was weighed

TABLE I

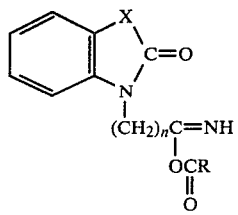

$$(CH_2)_nC=NH$$
$$|$$
$$OCR$$
$$\parallel$$
$$O$$

| Example No. | n | x | R | ml of Anhydride | Mp °C. | % Yield | % C Calcd | % C Found | % H Calcd | % H Found | % N Calcd | % N Found | % S Calcd | % S Found |
|---|---|---|---|---|---|---|---|---|---|---|---|---|---|---|
| 3 | 1 | S | —CH₃ | 200 | 203–4ᵃ | 94 | 49.61 | 49.64 | 3.78 | 3.78 | 10.52 | 10.52 | 24.08 | 24.04 |
| 4 | 1 | S | —C₂H₅ | 250 | 207ᵇ | 82 | 51.41 | 51.42 | 4.31 | 4.33 | 9.99 | 10.00 | 22.87 | 22.91 |
| 5 | 1 | S | —C₃H₇ | 250 | 172–4ᶜ | 68 | 53.04 | 53.31 | 4.79 | 4.55 | — | — | — | — |
| 6 | 2 | S | —CH₃ | 250 | 104–6 | 82 | 51.41 | 52.07 | 4.31 | 4.08 | 9.99 | 10.22 | — | — |
| 7 | 2 | O | —CH₃ | 150 | 124–6 | 76 | — | — | — | — | 10.60 | 10.96 | 12.13 | 12.52 |

ᵃRecrystallization from toluene
ᵇRecrystallization from methyl alcohol
ᶜRecrystallization from isopropyl alcohol/ethyl acetate (5:1)

One aspect of the present invention is the discovery that the reaction of the amide with the appropriate anhydride requires the use of a catalyst comprising an alkali metal salt of the acid corresponding to the anhydride. If a catalyst is not used, the product obtained is a mixture comprising three components, an imide, a nitrile and an unknown. Use of the catalyst, especially the sodium salt of the acid corresponding to the anhydride, significantly reduces the formation of the nitrile and the unknown resulting in a relatively pure product consisting of the desired imide.

In accordance with a second aspect of the present invention, imides derived from 2-thioxo-3-benzothiazoline acetic and propionic acid represented by formula (I) above wherein X is sulfur have been found to be effective herbicides. The compounds may be used by themselves or as the active ingredient in a herbicidal composition.

As used herein, the term "herbicidal active ingredient" is understood to mean an imide of the foregoing formula (I) wherein X is sulfur.

Control of undesirable weed growth may be obtained by applying the herbicidal active ingredient to the plant locus which is defined herein to include the growth medium surrounding the plant, the seeds, emerging seedlings, roots, stems, leaves, flowers and other plant parts. Application to the leaves or stems after the weed has emerged from the soil is preferred. This type of treatment is known to those skilled in the art as a post-emergent treatment.

To illustrate the herbicidal properties of the compounds of the present invention, said compounds were tested in the following manner.

The pre-emergent test was conducted as follows:

A good grade of top soil was placed in aluminum pans and compacted to a depth of 0.95 to 1.27 cm from the top of the pan. On the top of the soil was placed a predetermined number of seeds or vegetative propagules of various plant species which are compacted to soil level. The soil required to level fill the pans after seeding or adding vegetative propagules was weighed into a pan. A known amount of the herbicidal active ingredient applied in a solvent or as a wettable powder and the soil were thoroughly mixed, and used as a cover layer for prepared pans. After treatment, the pans were moved into a greenhouse bench where they were watered from below as needed to give adequate moisture for germination and growth.

As noted in Table II below, approximately 2 to 4 weeks after seeding and treating, the plants were observed to determine all deviations from the normal growth habit and the results recorded. A herbicidal rating code was used to signify the extent of the phytotoxicity of each species. The ratings are defined as follows:

| % Control | Rating |
|---|---|
| 0–24 | 0 |
| 25–49 | 1 |
| 50 74 | 2 |
| 75–100 | 3 |

The plant species utilized in these tests are identified by letter in accordance with the following legend: p0
A—Canada Thistle
B—Cocklebur
C—Velvetleaf
D—Morningglory
E—Lambsquarters
F—Smartweed
G—Yellow Nutsedge
H—Quackgrass
T—Johnsongrass
J—Downy Brome
K—Barnyardgrass Results of the pre-emergent tests are summarized in Table II below.

TABLE II

| Compound | WAT* | kg h | A | B | C | D | E | F | G | H | I | J | K |
|---|---|---|---|---|---|---|---|---|---|---|---|---|---|
| 3 | 2 | 5.6 | 3 | 1 | 0 | 0 | 0 | 0 | 0 | 0 | 0 | 0 | 0 |
| 4 | 4 | 11.2 | 2 | 2 | 2 | 1 | 1 | 1 | 0 | 0 | 0 | 0 | 0 |

TABLE II-continued

| Compound | WAT* | kg h | A | B | C | D | E | F | G | H | I | J | K |
|---|---|---|---|---|---|---|---|---|---|---|---|---|---|
| 5 | 2 | 11.2 | 2 | 1 | 2 | 1 | 1 | 1 | — | 0 | 0 | 0 | 0 |
| 6 | 2 | 11.2 | 0 | 0 | 0 | 0 | 3 | 0 | 0 | 0 | 0 | 0 | 0 |

*Weeks observed after treatment

The post-emergent tests were conducted as follows:

The herbicidal active ingredients are applied in spray form to two or three-week old specimens of various plant species. The spray, a solution or wettable powder suspension containing the appropriate rate of herbicidal active ingredient to give the desired test rate and a surfactant, is applied to the plants. The treated plants are placed in a greenhouse and approximately two or four weeks later the effects are observed and recorded. The results are shown in Table III in which the post-emergent herbicidal rating code is as follows:

| % Control | Rating |
|---|---|
| 0-24 | 0 |
| 25-49 | 1 |
| 50-74 | 2 |
| 75-99 | 3 |
| 100 | 4 |

The plant species utilized in these tests are identified by letter in accordance with the previous legend.

TABLE III

| Compound | WAT* | kg h | A | B | C | D | E | F | G | H | I | J | K |
|---|---|---|---|---|---|---|---|---|---|---|---|---|---|
| 3 | 2 | 5.6 | 0 | 1 | 1 | 1 | 2 | 0 | 0 | 0 | 0 | 0 | 0 |
| 4 | 2 | 11.2 | 1 | 2 | 1 | 1 | 2 | 0 | 0 | 0 | 0 | 0 | 0 |
| 5 | 2 | 11.2 | 0 | 2 | 0 | 1 | — | 0 | 0 | 0 | 0 | 0 | 0 |
| 6 | 2 | 11.2 | 0 | 0 | 0 | 0 | 0 | 0 | 0 | 0 | 0 | 0 | 0 |

*Weeks observed after treatment

The above tables illustrate one aspect of the present invention, that is, the use of the compounds of the invention to kill or injure undesirable plants, e.g., weeds. Another aspect of the invention, however, is the use of the imides of formula (I) for the regulation of desirable plant growth, especially leguminous plants such as soybeans. More particularly, the compounds of the foregoing formula (I) have been found to be effective in regulating the growth of leguminous plants.

As used herein, the regulation of "plant growth or development" is understood to mean the modification of the normal sequential development of a treated desirable plant to agricultural maturity. Such modifications are most readily observed as changes in size, shape, color or texture of the treated plant or any of its parts. Similarly, changes in the quantity of plant fruit or flowers are also quite apparent from visual inspection. The above changes may be characterized as an acceleration or retardation of plant growth, stature reduction, leaf or canopy alteration, increased branching, terminal inhibition, increased flowering, defoliation, increased root growth, increased cold hardiness and the like. While many of these modifications are desirable in and of themselves, most often it is their effect on the economic result that is of most importance. For example, a reduction in stature of the plant permits the growing of more plants per unit area. A darkening of the foliar color may be illustrative of higher chlorophyll activity indicative of improved rate of photosynthesis. Alteration of leaf shape and size as well as alteration of the canopy may allow more light to penetrate the lower leaves of the plant, thus improving the rate of photosynthesis.

Although the regulation of plant growth in accordance with the present invention may include partial inhibition of plant growth when used as a plant growth regulant, it does not include the total inhibition or killing of such plants. The present invention contemplates the use of an amount of the imide of formula (I) as the active ingredient in a plant growth regulating composition which will modify the normal sequential development of the treated plant to agricultural maturity. Such plant growth regulating amounts may vary, not only with the material selected, but also with the modifying effect desired, the species of plant and its stage of development, the plant growth medium and whether a permanent or a transitory effect is sought. It is, however, well within the skill of the art to determine the amount of active ingredient required.

Modification of the plants may be accomplished by applying the active ingredient to the plant locus which has been defined herein to include the growth medium surrounding the plant, the seeds, emerging seedlings, roots, stems, leaves, flowers, or other plant parts. Such application may be made directly to the plant part, or indirectly by application to the plant growth medium.

Utilizing the imide of formula (I) as the active ingredient in plant growth regulating compositions, said compounds were found to possess plant growth regulating activity when tested in accordance with the following procedure.

A number of soybean plants, variety Williams, were grown from seeds in plastic pots in the greenhouse for a period of one week at which time the plants are thinned to one plant per pot. When the second trifoliate leaf (three weeks) was fully expanded, the plants were treated with a solution of the active ingredient in acetone and water.

When the fifth trifoliate leaf (four or five weeks) was fully expanded, the treated plants were compared with the non-treated control plants and the observations recorded. Those observations are summarized in Table IV, below.

TABLE IV

| CP OF EX. NO. | RATE | OBSERVATIONS |
|---|---|---|
| 3 | 0.112 | leaf alteration, inhibition of dry weight |
|  | 0.56 | leaf alteration of old and new growth, leaf distortion, leaf inhibition, inhibition of dry weight, slight leaf burn |
|  | 2.80 | stature reduction, stem distortion, leaf distortion, leaf inhibition, leaf alteration |

TABLE IV-continued

| CP OF EX. NO. | RATE | OBSERVATIONS |
|---|---|---|
| | | of new growth, inhibition of dry weight, slight leaf burn |
| 4 | 0.112 | inhibition of dry weight |
| | 0.56 | leaf alteration of new growth, leaf distortion, leaf inhibition, inhibition of dry weight, slight leaf burn |
| | 2.80 | leaf alteration of old and new growth, leaf distortion, leaf inhibition, inhibition of dry weight, slight leaf burn |
| 5 | 0.112 | none |
| | 0.56 | leaf alteration of old and new growth, leaf inhibition, inhibition of dry weight, slight leaf burn |
| | 2.80 | leaf alteration of old and new growth, leaf inhibition, slight leaf burn |
| 6 | 0.112 | none |
| | 0.56 | none |
| | 2.80 | leaf distortion of old and new growth, inhibition of dry weight |
| 7 | 0.112 | stimulation of dry weight |
| | 0.56 | none |
| | 2.80 | leaf alteration of new growth |

As can be seen from the above data, the imide of formula (I) above is especially effective at rates of about 2.8 kilograms per hectare.

Thus, the above data illustrate that the compounds of the invention may be used as a herbicide or a plant growth regulant. When used as a herbicide, it is desirable that rates of application about 1.12 kilograms per hectare and above be utilized. When used to regulate the growth of desirable plants, rates below 5.6 kilograms per hectare, especially 0.56 or 2.8, are preferred.

In selecting the appropriate time and rate of application of th active ingredient, it will be recognized that precise rates will also be dependent upon the desired response, mode of application, plant variety, soil conditions and various other factors known to those skilled in the art. In addition, it will be recognized that single or multiple applications may be used to exert the desired response.

In the practice of the invention, the active ingredient, whether used as a herbicide or a plant growth regulant, can be used alone or in combination with other pesticides or a material referred to in the art as an adjuvant in either liquid or solid form. To prepare such compositions, the active ingredient is admixed with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely-divided particulate solid, a solvent liquid of organic origin, water, a wetting agent, dispersing agent or emulsifying agent or any suitable combination of these.

Illustrative finely-divided solid carriers and extenders which are useful in plant growth regulating compositions of this invention include the talcs, clays, pumice, silica, diatomaceous earth, quartz, Fullers earth, sulfur, powdered cork, powdered wood, walnut flour, chalk, tobacco dust, charcoal and the like. Typical liquid diluents include Stoddard solvent, acetone, alcohols, glycols, ethyl acetate, benzene and the like. The plant growth regulating compositions of this invention, particularly liquids and wettable powders, usually contain one or more surface-active agents in amounts sufficient to render a given composition readily dispersible in water or in oil. The term "surface-active agent" is understood to include wetting agents, dispersing agents, suspending agents and emulsifying agents. Such surface-active agents are well known and reference is made to U.S. Pat. No. 2,547,724, columns 3 and 4, for detailed examples of the same.

Generally, the active ingredients are applied in the form of a composition containing one or more adjuvants which aid in the application of a uniform distribution of the active ingredient. The application of liquid and particulate solid compositions of the active ingredient can be carried out by conventional techniques utilizing, for example, spreaders, power dusters, boom and hand sprayers and spray dusters. The composition can also be applied from airplanes as a dust or spray.

Compositions of this invention, whether used as a herbicide or a plant growth regulant, generally contain from about 5 to 95 parts active ingredient, about 1 to 50 parts surface-active agent and about 4 to 94 parts solvents, all parts being by weight based on the total weight of the composition.

Although this invention has been described with respect to specific modifications, the detals thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A method for preventing the growth of undesirable plants which comprises applying to the plant locus a herbicidally effective amount of a compound having the formula

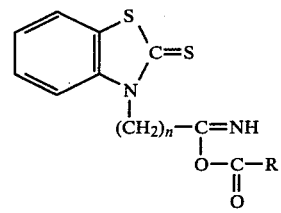

where R is a lower alkyl and n is 1 or 2.

* * * * *

UNITED STATES PATENT AND TRADEMARK OFFICE
CERTIFICATE OF CORRECTION

PATENT NO. : 4,362,547

DATED : December 7, 1982

INVENTOR(S) : John J. D'Amico

It is certified that error appears in the above-identified patent and that said Letters Patent is hereby corrected as shown below:

At Columns 3-4, in Table I, in the structural formula given for the imide derivatives of the 2-thioxo-3-benzox(thia)azoline compounds, at the 2-position of the ring the "carbonyl" group should be a --thiocarbonyl-- group. Thus, the formula should be as follows:

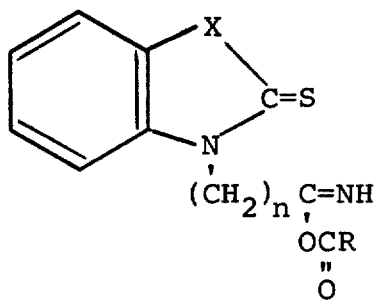

Signed and Sealed this

Fourth Day of September 1984

[SEAL]

Attest:

GERALD J. MOSSINGHOFF

Attesting Officer

Commissioner of Patents and Trademarks